(12) United States Patent
Butler et al.

(10) Patent No.: US 9,149,303 B2
(45) Date of Patent: Oct. 6, 2015

(54) POSTERIOR SPINAL PROSTHESIS

(71) Applicant: Life Spine, Inc., Hoffman Estates, IL (US)

(72) Inventors: Michael S. Butler, St. Charles, IL (US); Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 14/157,238

(22) Filed: Jan. 16, 2014

(65) Prior Publication Data

US 2014/0135846 A1  May 15, 2014

Related U.S. Application Data

(63) Continuation of application No. 12/492,668, filed on Jun. 26, 2009, now Pat. No. 8,663,295.

(60) Provisional application No. 61/076,284, filed on Jun. 27, 2008.

(51) Int. Cl.
*A61B 17/80* (2006.01)
*A61B 17/70* (2006.01)

(52) U.S. Cl.
CPC ......... *A61B 17/7058* (2013.01); *A61B 17/7032* (2013.01)

(58) Field of Classification Search
USPC .......................................... 606/280, 286–297
See application file for complete search history.

(56) References Cited

U.S. PATENT DOCUMENTS

| | | | |
|---|---|---|---|
| 5,092,893 A | 3/1992 | Smith | |
| 5,209,752 A | 5/1993 | Ashman et al. | |
| 5,531,747 A | 7/1996 | Ray | |
| 7,967,851 B2 | 6/2011 | Bickley et al. | |
| 2001/0047172 A1 | 11/2001 | Foley et al. | |
| 2003/0153913 A1 | 8/2003 | Altarac et al. | |
| 2005/0149021 A1 | 7/2005 | Tozzi | |
| 2005/0234456 A1 | 10/2005 | Malandain | |
| 2006/0004363 A1 | 1/2006 | Brockmeyer et al. | |
| 2007/0118121 A1 | 5/2007 | Purcell et al. | |
| 2009/0177234 A1 | 7/2009 | Butler et al. | |

OTHER PUBLICATIONS

International Search Report for Application No. PCT/US2009/048865, mail date Aug. 12, 2009, 3 pages.

*Primary Examiner* — David Isabella
*Assistant Examiner* — Christine Nelson
(74) *Attorney, Agent, or Firm* — Foley & Lardner LLP

(57) ABSTRACT

A posterior spinal prosthesis is configured to cover exposed portions of a spinal column especially, but not necessarily, as a result of a medical spinal procedure and particularly, to provide posterior coverage of an exposed spinal cord, soft tissue, Foramen and/or adipose tissue, associated with one or more vertebrae as a result of the removal the spinous processes and/or the spinous process and laminar hoods from the one or more vertebrae of the spine as a result of a spinal decompression procedure or other reason. A plate forming the prosthesis is connectable to spine rod constructs implanted on lateral sides of the vertebrae and projects in the posterior direction relative to the connection. The plate is generally curved in the superior/inferior direction to provide either a lordotic or kyphotic curvature depending on the portion of the spine to which the prosthesis is utilized. As such, the posterior spinal prosthesis may be used on any portion of the spine such as the cervical vertebrae, the thoracic vertebrae and/or the lumbar vertebrae. The present posterior spinal prosthesis also provides posterior stabilization of the associated vertebrae as well as aiding in preventing post operative soft tissue cavitation at the decompression site.

15 Claims, 7 Drawing Sheets

POSTERIOR SPINAL PROSTHESIS

RELATED APPLICATIONS

This patent application is a continuation of U.S. patent application Ser. No. 12/492,668 filed on Jun. 26, 2009, which claims the benefit of and/or priority to U.S. Provisional Patent Application No. 61/076,284 filed on Jun. 27, 2008, each of which are hereby incorporated herein by reference in their entireties.

BACKGROUND OF THE INVENTION

1. Field of the Invention

The present invention relates to spinal devices and, in particular, to spinal prostheses for use with spinal fixation devices, assemblies and systems such as spinal screw and rod assemblies or systems that are attached onto a patient's spine.

2. Background Information

There are many medical situations, because of disease, injury or deformity, where it is necessary to align, hold and/or fix a desired relationship between adjacent vertebral bodies. In order to accomplish this goal, orthopedic spinal surgeons utilize spinal fixation devices, systems and/or assemblies to provide the desired relationship between adjacent vertebral bodies. Such spinal fixation devices typically include one or more spinal fixation elements, such as relatively rigid fixation rods, that are connected to adjacent vertebrae by attaching the rod to anchor devices, systems and/or assemblies affixed onto the vertebrae. The anchor devices are typically spinal bone screw assemblies that include bone screws and screw head/spinal rod connectors.

The spinal fixation rods are typically placed on opposite sides of the spinous processes of adjacent vertebrae in a substantially parallel relationship. Spinal fixation rods may have pre-determined contours according to properties of the target implantation site. Once installed, the spinal fixation rods hold the vertebrae in a desired spatial relationship. It may also be necessary in some circumstances to provide a spinal cross-connector at one or more points between the two spinal fixation rods in order to provide additional stability to the structure. Particularly, adjacent spinal fixation rod assemblies can be made more robust by using a cross-connector to bridge the pair of spinal rods. Current cross-connectors are generally rods themselves that are adapted for connection at ends thereof to the spinal rods.

There are various medical spinal procedures where cross-connectors or current spinal prostheses of any kind do not address all of the issues created by the various medical spinal procedures. One such medical spinal procedure is a spinal decompression procedure. Spinal decompression is achieved in the patient by the removal of several adjacent spinous processes and the elongation and/or stabilization of the adjacent vertebrae through the use of the spinal fixation assemblies such as indicated above (i.e. spinal rods and spinal bone screw/rod holder assemblies). This procedure, however, can contribute to overexposure of the vulnerable spinal cord as well as create the potential for post operative soft tissue cavitation. While current cross-connectors may be used for stabilization of the spinal fixation assemblies (and thus the affected vertebrae), they are not adequate to address overexposure of the vulnerable spinal cord or the potential for post operative soft tissue cavitation as a result of a spinal decompression procedure. Other known spinal devices also do not address these problems. Moreover, other medical spinal procedures may overexpose portions of the spinal cord or spinal cord area as well as create the potential for post operative soft tissue cavitation of which the known spinal devices do not address.

Accordingly, there presently exists a need for a spinal prosthesis that addresses the inadequacies of the prior art.

SUMMARY OF THE INVENTION

The present invention is a posterior spinal prosthesis having a body that extends over and covers posterior portions of a spine. The posterior spinal prosthesis can cover exposed portions of the spine especially, but not necessarily, as a result of a medical spine procedure. The posterior spinal prosthesis may be used on any portion of the spine such as the cervical vertebrae, the thoracic vertebrae and the lumbar vertebrae.

The posterior spinal prosthesis is connectable to one or more spine implants or implant constructs (collectively, 'spine implants') that have been attached to one or more vertebrae of the spine. The spine implants are situated generally, but not necessarily, on lateral sides of the posterior portion of the vertebrae. Such spine implants include, but are not limited to, spine rods, spine rod assemblies/constructs, vertebral bone screws and vertebral bone screw and spine rod holder/connector assemblies/constructs.

The body has a plate, hood, platform, cover or the like (collectively, 'plate') that extends over posterior portions or areas of the vertebrae. Fixation elements associated with the body allow coupling of the plate to the spine implants. The plate is configured so as to project in the posterior direction relative to portions of the fixation elements. In one form, the fixation elements are flanges formed on either side of the plate. The flanges are configured to receive a connector that provides coupling of the body to the spine implants, allow for direct connection of the plate to one or more vertebrae or include a connector that provides coupling of the body to the spine implants. The fixation elements may take other forms as desired.

The present posterior spinal prosthesis is thus adapted to provide posterior coverage of an exposed spinal cord, soft tissue, Foramen and/or adipose tissue, of one or more vertebrae as a result of the removal the spinous processes and/or the spinous process and laminar hoods from one or more vertebrae of the spine such as for a spinal decompression procedure or other reason. The posterior spinal prosthesis also provides posterior stabilization of the associated vertebrae as well as aiding in preventing post operative soft tissue cavitation at the decompression site.

The posterior spinal prosthesis is formed of a suitable biocompatible material that is preferably, but not necessarily, a biocompatible plastic such as PEEK (polyetheretherketone). Of course, other biocompatible plastics or materials such as metal may be used. The posterior spinal prosthesis may also be formed of a biocompatible plastic with the incorporation of a biocompatible metal such as titanium. Furthermore, the posterior spinal prosthesis may be formed entirely of a biocompatible metal such as titanium. The posterior spinal prosthesis may be made in various sizes or sizing platforms in order to accommodate a variety of anatomies. As such, the body may be formed as a single or unitary piece or may be formed as multiple pieces. A multiple piece (i.e. two or more piece) posterior spinal prosthesis may provide accommodation for differing widths between spine implants such as spinal rods for interconnection.

In a particular embodiment, the body (whether a single or multi-piece body) is characterized by the plate having flanges at lateral sides thereof. The lateral sides are curved, each forming a bend relative to a level defined by the plate, with the flanges disposed at the end of the bends. The configuration of the plate, the curved lateral sides and their respective flanges, form a pocket, area, channel or the like.

In one form, the first flange has an elongated slot extending in the superior/inferior or longitudinal direction with the first slot defining an elongated first outer edge. The second flange likewise has an elongated slot extending in the superior/inferior or longitudinal direction with the second slot defining an elongated second outer edge. The plate is at a level relative to a level of the first and second flanges that generally corresponds in height to that of the removed spinous processes such that, when installed, the plate is posterior to the flanges.

In one form, the flanges each have an undercut or groove on the underside thereof about the respective slots. The grooves are sized to provide a trough or channel that receives a connector or spine implant component for mounting the posterior spinal prosthesis. The connector or spine implant component translates in the groove to allow variable attachment of the body to the spine implant.

The body of the posterior spinal prosthesis may moreover be curved from the superior end or side to the inferior end or side. This curvature may be lordotic as in the case of cervical and lumbar posterior spinal prostheses or kyphotic as in the case of thoracic posterior prostheses.

The present invention provides coverage of exposed spinal cord areas, aids in posterior stabilization, and aids in preventing post operative soft tissue cavitation by providing anatomically accurate preservation to the cervical, thoracic and/or lumbar regions of the spine.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A detailed description of the features, functions and/or configuration of the prosthesis depicted in the figures will now be presented. It should be appreciated that not all of the features of the prosthesis of the figures are necessarily described. These non discussed features as well as discussed features are inherent from the figures. Other non discussed features may be inherent in geometry and/or configuration of the prosthesis.

DETAILED DESCRIPTION OF AN EMBODIMENT OF THE INVENTION

Figure 1:
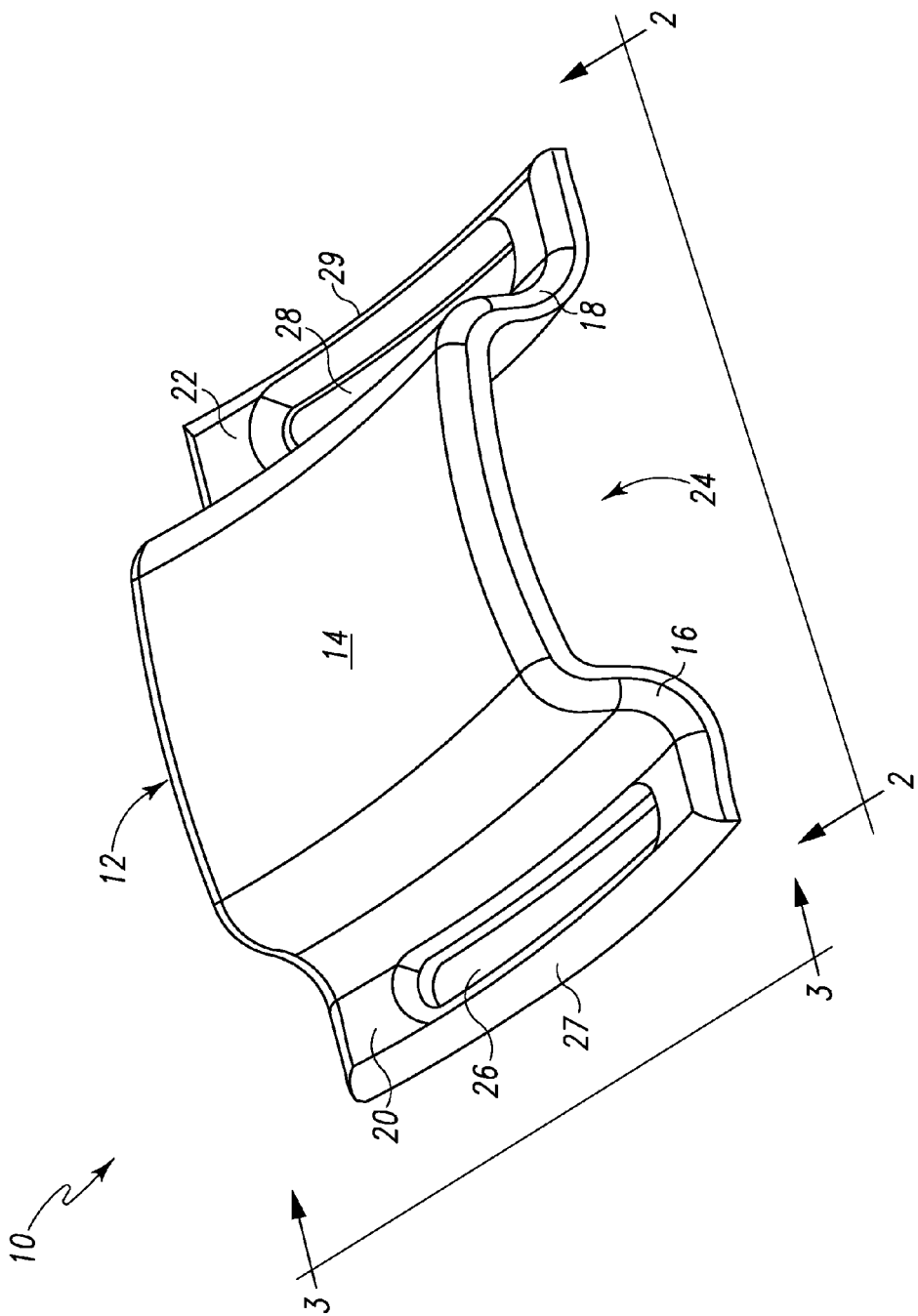
FIG. 1 is a perspective view of an exemplary posterior spinal prosthesis fashioned in accordance with the present principles.
Figure 2:
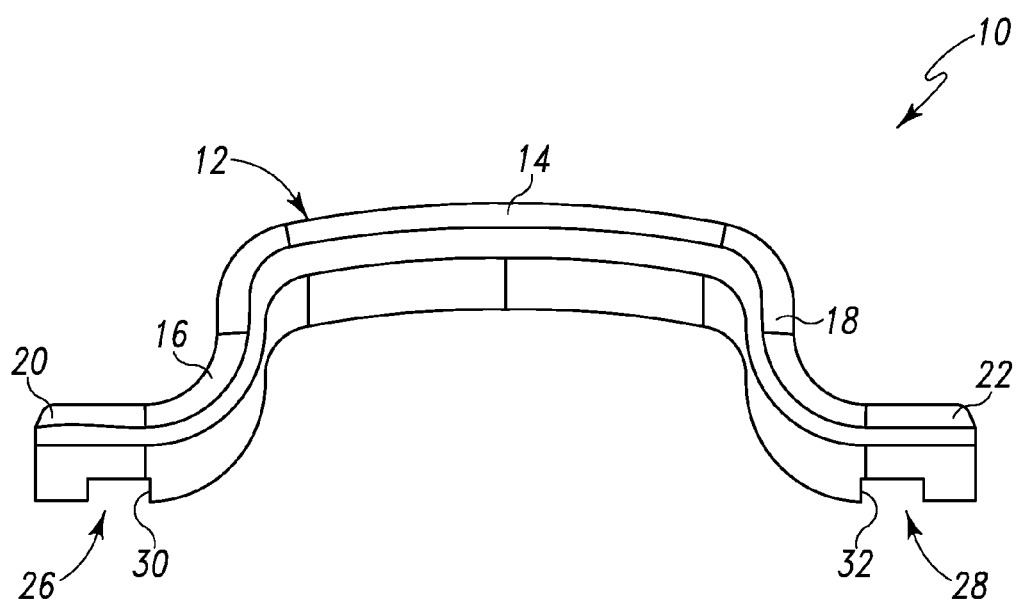
FIG. 2 is a front view of the posterior spinal prosthesis of FIG. 1 taken along line 2-2 thereof.
Figure 3:
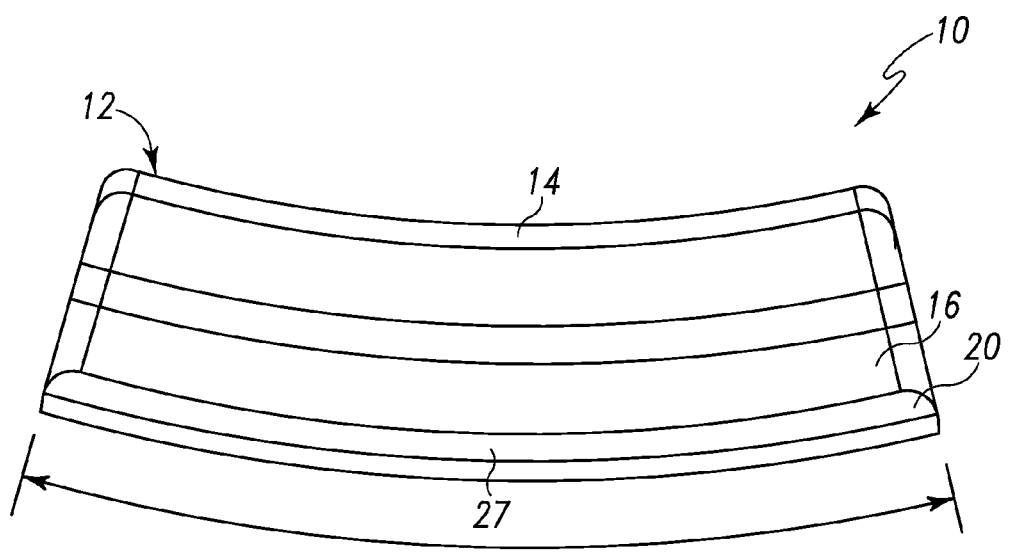
FIG. 3 is a side view of the posterior spinal prosthesis of FIG. 1 taken along line 3-3 thereof.

Referring to FIGS. 1-3 there is depicted an exemplary embodiment of a posterior spinal prosthesis, generally designated 10, fashioned in accordance with the present principles. It should be appreciated that the present posterior spinal prosthesis may be used for any portion of the spine such as on the cervical vertebrae, the thoracic vertebrae and/or the lumbar vertebrae. However, the present posterior spinal prosthesis is shown and described with reference to the cervical vertebrae. The present spinal prosthesis 10 is adapted to provide posterior coverage of an exposed spinal cord, soft tissue, Foramen and/or adipose tissue, of one or more vertebrae as a result of the removal the spinous processes and/or the spinous process and laminar hoods from one or more vertebrae of the spine such as for a spinal decompression procedure. The posterior spinal prosthesis also provides posterior stabilization of the associated vertebrae as well as aiding in preventing post operative soft tissue cavitation.

The posterior spinal prosthesis 10 is formed by a body 12 that is made of a biocompatible material of sufficient strength for the present application. The posterior spinal prosthesis 10 is formed of a biocompatible material. Preferably, but not necessarily, the present posterior spinal prosthesis 10 is formed of a biocompatible plastic such as PEEK (polyetheretherketone). Other biocompatible plastics or materials such as metal may be used. The posterior spinal prosthesis 10 may also be formed of a biocompatible plastic with the incorporation of a biocompatible metal such as titanium. Furthermore, the spinal prosthesis may be formed entirely of a biocompatible metal such as titanium. Other biocompatible materials may be used as desired. It should be appreciated that the present spinal prosthesis 10 may be made in various sizes or sizing platforms in order to accommodate a variety of spine anatomies.

In the present embodiment, the body 12 is characterized by a plate, platform, cover, hood or hood portion 14 (collectively, 'plate 14') having a first curved side 16 and a second curved side 18 that is disposed opposite to the first curved side 16, the nomenclature first and second being arbitrary. The first curved side 16 is formed as a generally 180° bend relative to a plane defined by the hood 14. The second curved side 18 is also formed as a generally 180° bend relative to the plane of the hood 14. The body 12 is further defined by a first flange 20 that extends from an end of the first curved side 16 and is generally co-planar with the plane of the plate 14. Likewise, the body 12 is further defined by a second flange 22 that extends from an end of the second curved side 18 and is generally co-planar with the plane of the plate 14. The configuration of the plate 14, the first and second curved sides 16, 18 and their respective ends 20, 22 form a pocket, area, channel or the like 24. The superior/inferior length, size or distance of the body 12 (i.e. the length between the pointing arrows of line 3-3 of FIG. 1) is sized to cover a posterior area of the spine previously covered by one or more spinous processes.

As best seen in FIG. 1, the first flange 20 has a fixation element defined as an elongated slot 26 (first slot 26) extending in the superior/inferior or longitudinal direction. The first slot 26 defines an elongated first outer edge 27 of the first flange 20. The second flange 22 likewise has a fixation element defined as an elongated slot 28 (second slot 28) extending in the superior/inferior or longitudinal direction. The second slot 28 defines an elongated second outer edge 29. The lateral length, size or distance of the body 12 (i.e. the length between the pointing arrows of line 2-2 of FIG. 1) is sized to extend from the left side pedicle of the vertebra to the right side pedicle of the vertebra (as view in the figures).

The plate 14 is also disposed at a level or height relative to the first and second flanges 20, 22 that corresponds to the height of the removed spinous processes of the vertebra which the spinal prosthesis 10 will cover. In this regard, various spinal prostheses may be formed each having a different flange to plate height. Additionally, the body 12 may be formed such that the height of the plate may be adjustable such as in a multi-piece (i.e. two or more piece) posterior spinal prosthesis.

Referring particularly to FIG. 3, it can be seen that the body 12 is curved from the superior end or side to the inferior end or side. This particular curvature (i.e. a lordotic curve) mimics the natural curvature of the cervical portion of the spine. As well, a lordotic curvature is provided for lumbar posterior spinal prostheses. Various bodies 12 may be fashioned having various lordotic curvatures to accommodate differing anatomies. Moreover, the body 12 may be formed with a kyphotic curvature for thoracic applications. Again, various bodies 12 may be fashioned having various kyphotic curvatures to accommodate differing anatomies.

In FIG. 2 it can be seen that the body 12 has further features to allow the prosthesis 10 to be coupled or connected to a spine implant. Particularly, a first undercut or groove 30 is defined on the underside of the first flange 20 about the first slot 26. A second undercut or groove 32 is defined on the underside of the second flange 22 about the second slot 28. The first groove 30 is sized to provide a trough or channel. The first groove allows the reception of a first spine rod therein, a first spine implant component therein, or a first connector therein for mounting the spinal prosthesis 10. The first groove 30 also allows translation of the component or connector therein and/or the translation of the body 12 on the first spinal rod. Likewise, the second groove 32 is sized to provide a trough or channel. The second groove allows the reception of a second spine rod therein, a second spine implant component therein, or a second connector therein for mounting the spinal prosthesis 10. The second groove 32 also allows translation of the component or connector therein and/or the translation of the body 12.

Figure 4:
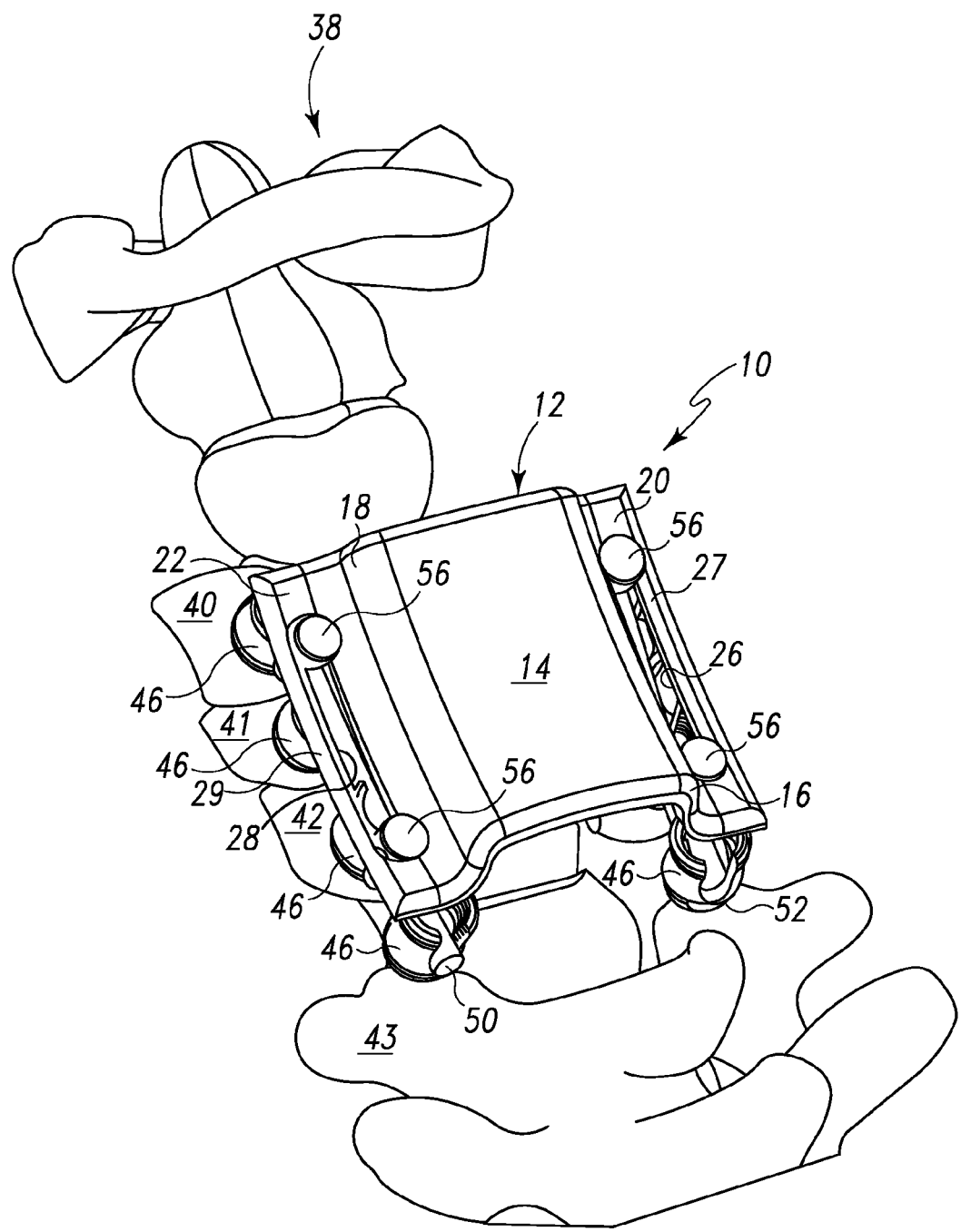
FIG. 4 is a perspective view of a section of the cervical portion of a human spine having a 3-level polyaxial spine screw and rod system (spinal rod and screw assembly) thereon with a posterior spinal prosthesis of the present invention installed thereon.

FIG. 4 illustrates a cervical spine portion 38 of a spine wherein the posterior spinal prosthesis 10 of FIGS. 1-3 affixed to a spinal fixation construct consisting of a three level (3-L) polyaxial spinal screw/rod assembly. The posterior spinal prosthesis 10 and the polyaxial spine screw/rod assembly may be considered a spinal plating assembly. Note that In FIG. 4, the posterior spinal prosthesis 10 has been rotated 180° relative to the views of FIGS. 1-3 in order to illustrate the symmetric nature of the prosthesis 10. Particularly, FIG. 4 illustrates a posterior spinal prosthesis 10 implanted in response to a spinal decompression procedure and, more particularly, as used in a cervical spinal decompression procedure. FIG. 4 shows four (4) cervical vertebrae labeled 40, 41, 42 and 43 wherein the spinous processes of two (2) of the vertebrae (not seen but are vertebra 41 and 42) have been removed. An area is thus defined where the vertebral bone of the spinous processes used to be. The 3-L polyaxial spine screw and rod system (spinal rod and screw assembly) is affixed to the vertebrae 40-43 such as is known in the art. The 3-L polyaxial spine screw and rod system is formed of a left side portion and a right side portion (as viewed in the figures). The left side portion holds a spinal rod 50 while the right side portion holds a spinal rod 52. Each one of the left and right side portions of the 3-L polyaxial spine screw and rod system holds the respective spinal rod through a plurality of vertebral bone screw assemblies each consisting of a vertebral bone screw (not seen) and a rod connector or screw head 46. A vertebral bone screw is affixed to a pedicle area of a vertebra while each rod connector/screw head 46 retains a portion of the spinal rod. The respective spinal rod is retained in a rod connector/screw head 60 by rod retention nut (not seen) that is received in the rod connector/screw head 46. The 3-L polyaxial spine screw and rod system is thus disposed on either side of the exposed area once formerly closed by the spinous processes and laminar hoods.

The posterior spinal prosthesis 10 is attached to the 3-L polyaxial spine screw and rod system through retention caps (connectors) 56 that extend through respective channels 26 and 28 of the spinal prosthesis 10 and are attached to the respective spinal rod 50 or 52. In this manner the posterior spinal prosthesis 10 may be positioned along the length of the spinal rods 50, 52, the spinal rods acting as rails for the reception of the posterior spinal prosthesis 10.

It should be appreciated that while the present posterior spinal prosthesis 10 is shown in use and discussed herein with respect to the cervical portion of the spine, the present posterior spinal prosthesis 10 may be used with respect to other portions of the spine such as the thoracic and/or lumbar portions. The present posterior spinal prosthesis 10 may also be used for reasons other than those mentioned herein and or for medical spinal procedures other than spinal decompression.

Figure 5:
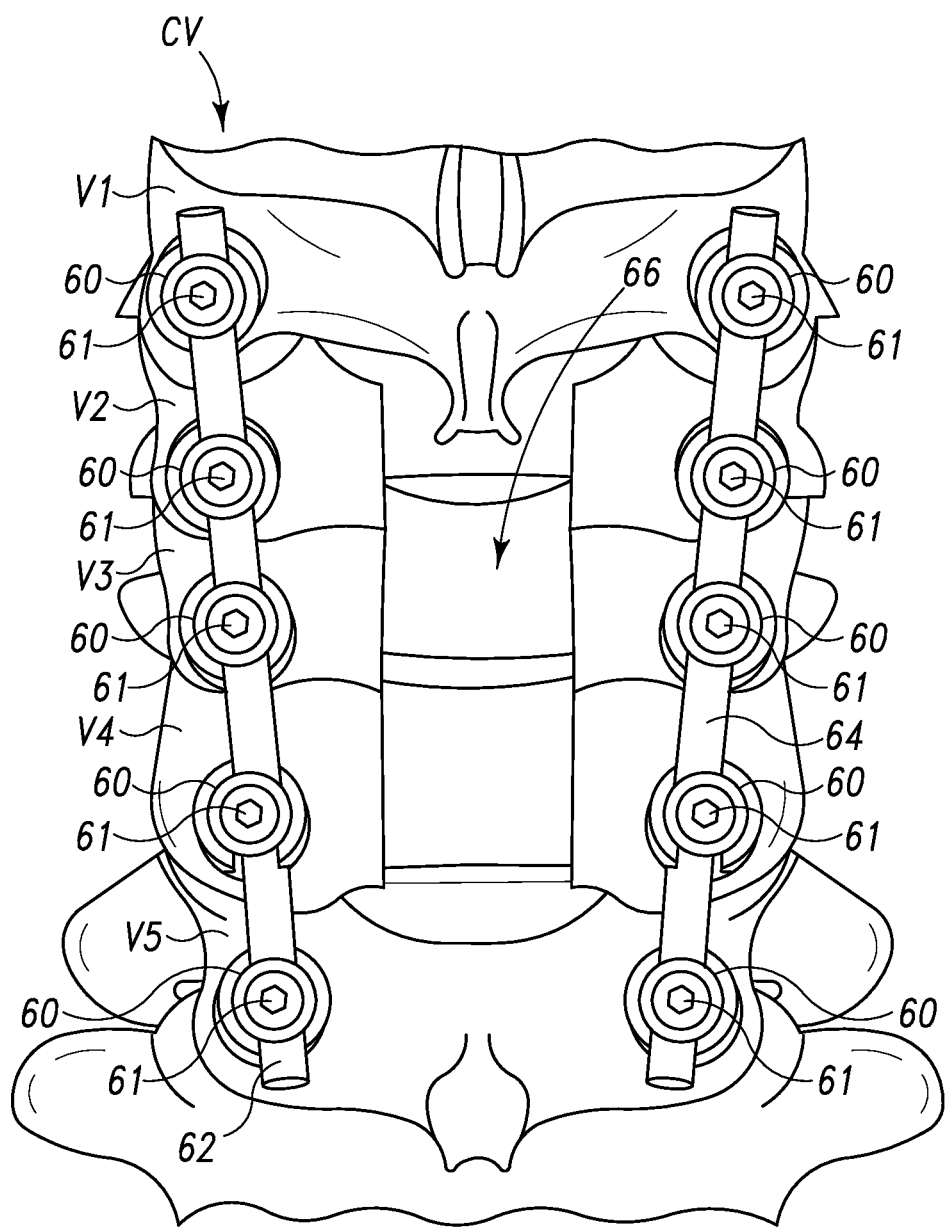
FIG. 5 is a posterior plan view of a cervical spine portion of a human spine having undergone decompression wherein the spinous processes and laminar hood of three (3) adjacent vertebrae have been removed and a four level (4-L) posterior cervical polyaxial spinal screw/rod assembly/system has been installed.

FIGS. 5-8 illustrate the use of the present posterior spinal prosthesis 10 in a spinal decompression procedure and, more particularly, as used in a cervical spinal decompression procedure. It should be appreciated that the spinal decompression procedure may be performed on the thoracic or lumbar portions of the spine. FIG. 5 shows five (5) vertebrae labeled V1, V2, V3, V4 and V5 of the cervical vertebrae CV of a spine wherein the spinous processes and laminar hoods of three (3) of the vertebrae V2, V3 and V4 have been removed. An area 66 is thus defined where the vertebral bone of the spinous processes used to be. A 4-level polyaxial spine screw and rod system (spinal rod and screw assembly) is affixed to the vertebrae V1-V5 such as is known in the art. The 4-level polyaxial spine screw and rod system is formed of a left side portion and a right side portion (as viewed in the figures). The left side portion holds a spinal rod 62 while the right side portion holds a spinal rod 64. Each one of the left and right side portions of the 4-level polyaxial spine screw and rod system holds the respective spinal rod through a plurality of vertebral bone screw assemblies each consisting of a vertebral bone screw (not seen) and a rod connector or screw head 60. A vertebral bone screw is affixed to a pedicle area of a vertebra while each rod connector/screw head 60 retains a portion of the spinal rod. The respective spinal rod is retained in a rod connector/screw head 60 by a rod retention nut 61 that is received in the rod connector/screw head 60. The 4-level polyaxial spine screw and rod system is thus disposed on either side of the exposed area 66 once formerly closed by the spinous processes and laminar hoods.

Figure 6:
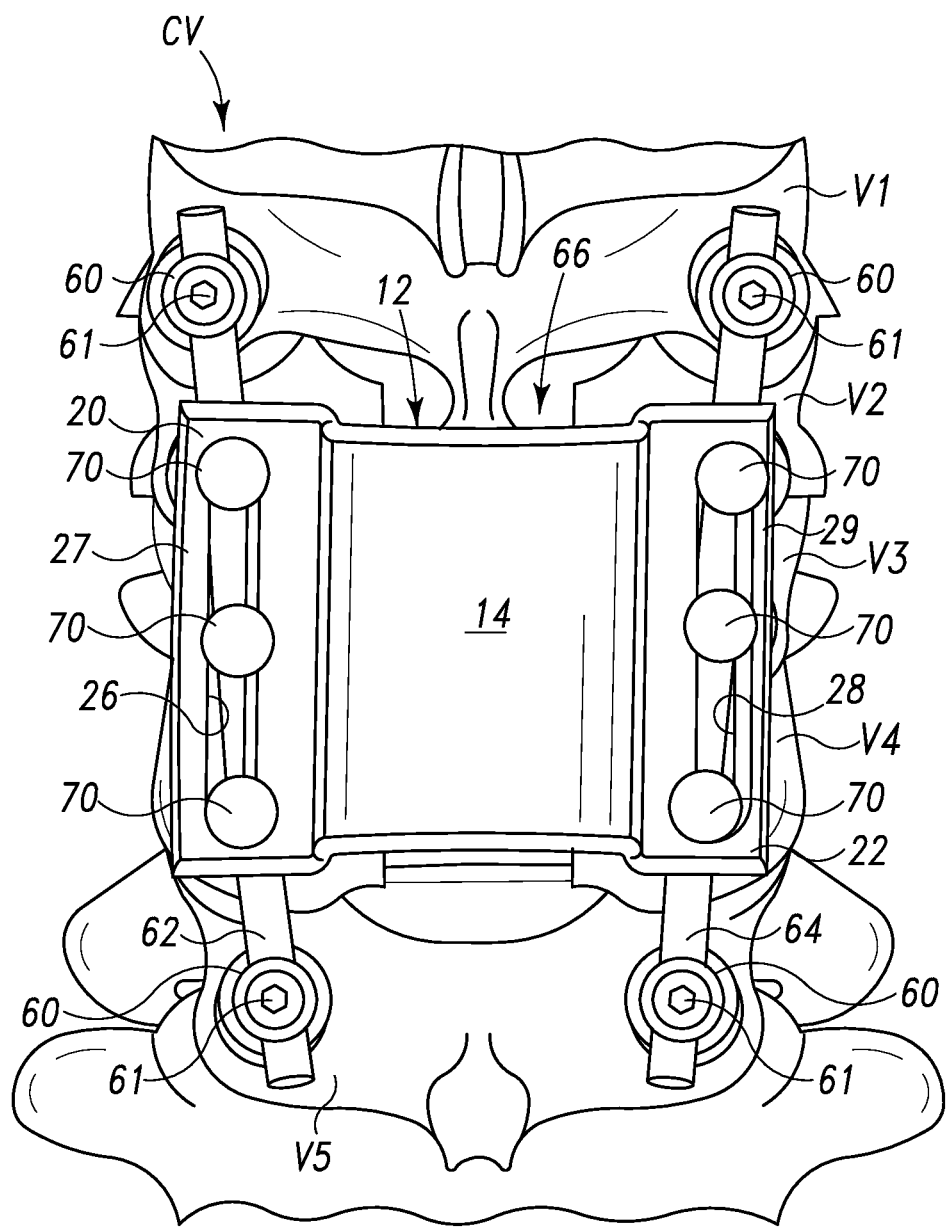
FIG. 6 is the posterior plan view of the decompressed cervical spine portion of a human spine of FIG. 5 with a posterior spinal prosthesis installed onto the 4-L posterior cervical polyaxial spinal screw/rod system/assembly.

FIG. 6 shows the posterior spinal prosthesis 10 affixed to the 4-level polyaxial spine screw and rod system such that the spinal prosthesis 10 is over the exposed area 66. In this example, the posterior spinal prosthesis 10 thus serves as a posterior cervical plate or spinous process prosthesis that provides coverage of the exposed area 66 (the exposed spinal cord and laminar hood) as a result of the cervical decompression procedure. The posterior spinal prosthesis 10 is attached to the polyaxial spine screw and rod system through retention caps 70 that extend through respective channels 26 and 28 of the posterior spinal prosthesis 10 and are attached to the screw heads/rod connectors 60 (and/or the rod retention nuts 61 thereof).

Figure 7:
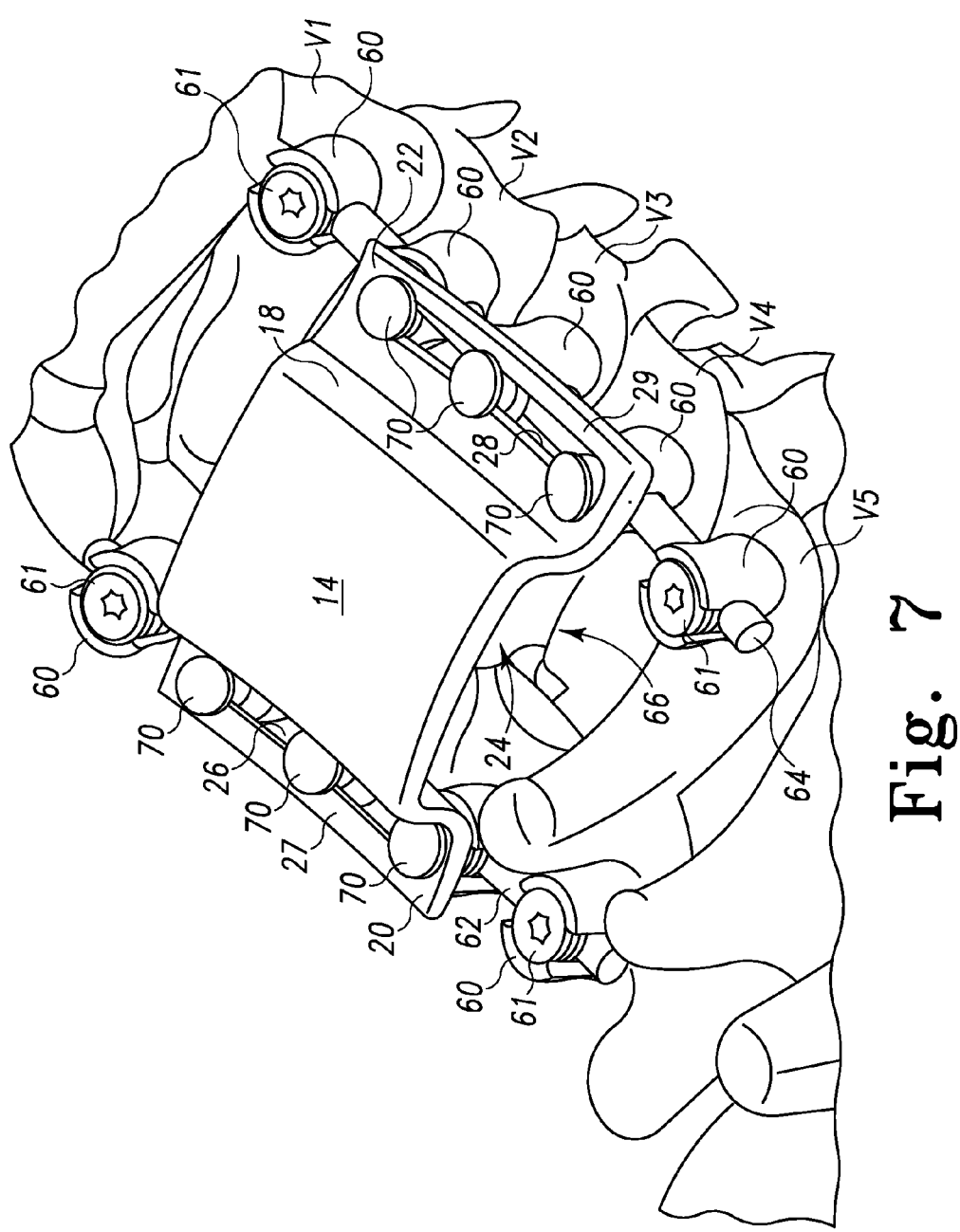
FIG. 7 is an enlarged side perspective view of the present posterior spinal prosthesis installed onto the posterior cervical polyaxial spinal screw/rod system/assembly as depicted in the view of FIG. 6.
Figure 8:
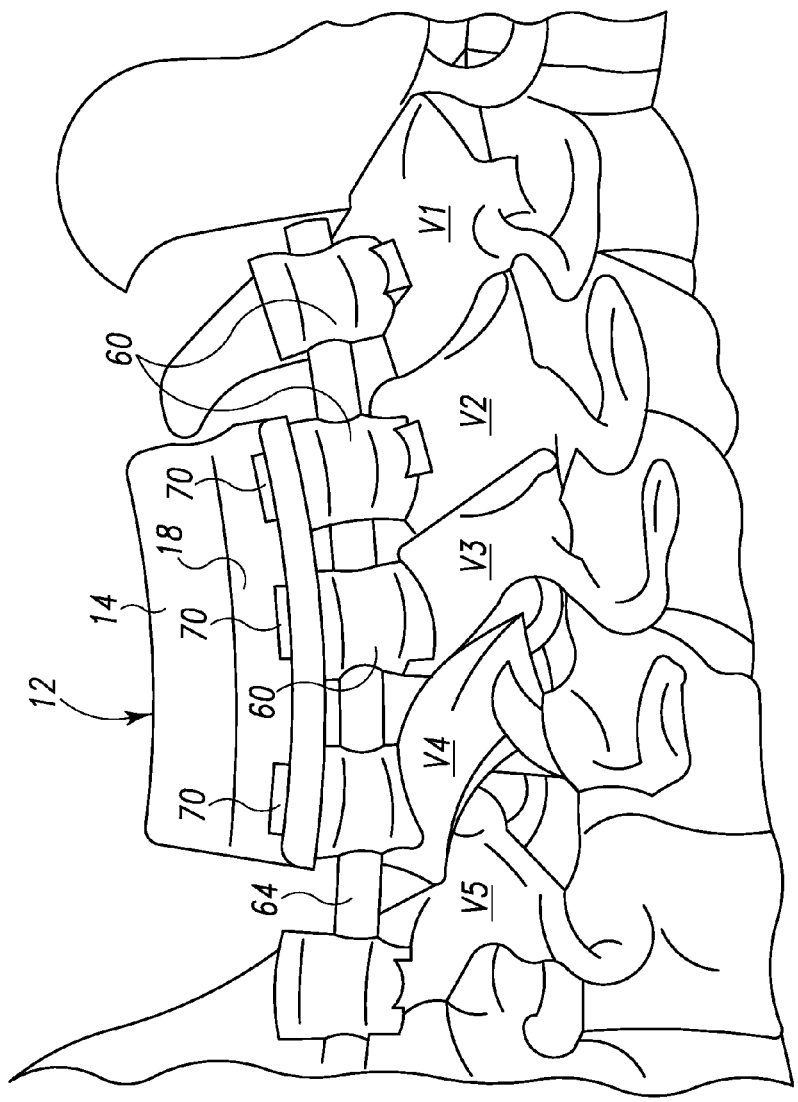
FIG. 8 is a side view of the present posterior spinal prosthesis installed onto the posterior cervical polyaxial spinal screw/rod system/assembly as depicted in the view of FIG. 6.

FIGS. 7-8 illustrate other views of the spinal plating system shown in FIG. 6. In FIG. 7 it can be seen that the posterior spinal plate 10 essentially completely covers the exposed area 66 from the superior end thereof to the inferior portion thereof. As seen in FIG. 8, the profile or height of the posterior spinal plate 10 is essentially the same as the profile or height of the removed spinous processes of the vertebrae. Therefore, the present posterior spinal prosthesis 10 may also be considered a spinous process prosthesis providing lordotic coverage of the spine. Additionally, as best seen in FIG. 8, the posterior spinal plate 10 is curved in like manner as the natural curvature of the particular portion of the spine.

It should be appreciated that while the posterior spinal prosthesis 10 is shown utilizing a spinal implant (as defined above) to provide a connection interface or point of connection of the body 12 onto or relative to the vertebrae, the body 12 may be connected or attached directly to one or more vertebrae. In this manner, bone screws or the like would be used to extend through the body 12, into the vertebral body and hold the prosthesis 10 to the vertebrae. Other manners of connection are also possible and contemplated. This provides a prosthesis that covers both the vertebrae and the spinal rods/rod assemblies.

The posterior spinal prosthesis 10 is contemplated to be made in different sizes to accommodate different anatomies and/or situations or procedures. Additionally, the posterior spinal prosthesis 10 may be made having varying superior/inferior curvatures.

Moreover, the present posterior spinal prosthesis 10 may be used with spine or spinal fixation systems other than those shown herein. As well, the present posterior spinal prosthesis 10 may be used for other spine or spinal purposes.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A posterior spinal device coupled to a first lateral posterior side of a plurality of vertebrae and to a second lateral posterior side of the plurality of vertebrae, the posterior spinal device comprising:
a first spinal fixation assembly coupled to the first lateral posterior side of the plurality of vertebrae;
a second spinal fixation assembly coupled to the first lateral posterior side of the plurality of vertebrae;
a plate sized to extend between the first and second lateral posterior sides of the plurality of vertebrae, the plate defining a first height and having a first lateral edge and a second lateral edge;
a first flange configured for connection directly to the first spinal fixation assembly coupled to the first posterior lateral side of the plurality of vertebrae, the first flange extending alongside the first lateral edge of the plate at a second height that is offset from the first height in an anterior direction, the first flange comprising a first elongated slot extending through the first flange;
a second flange configured for connection to the second spinal fixation assembly coupled to the second posterior lateral side of the plurality of vertebrae, the second flange extending alongside the second lateral edge of the plate at the second height that is offset from the first height in an anterior direction, the second flange comprising a second elongated slot extending through the second flange;
a first side member connecting the first flange to the first lateral side of the plate;
a second side member connecting the second flange to the second lateral side of the plate;
a plurality of first connectors extending through the first elongated slot to couple the plate to the first spinal fixation assembly at a plurality of positions along the first flange;
a plurality of second connectors extending through the second elongated slot to couple the plate to the second spinal fixation assembly at a plurality of positions along the second flange;
wherein the plate is located between the first flange and the second flange and generally parallel to the first flange and the second flange across a lateral direction to at least partially cover the plurality of vertebrae.

2. The posterior spinal device of claim 1, wherein:
the first spinal fixation assembly comprises a first spinal rod coupled to at least one connector/screw head, and the plurality of first connectors are coupled directly to the first spinal rod; and
the second spinal fixation assembly comprises a second spinal rod coupled to at least one connector/screw head, and the plurality of second connectors are coupled directly to the second spinal rod.

3. The posterior spinal device of claim 1, wherein:
the first first spinal fixation assembly comprises a spinal rod coupled to at least one connector/screw head, and the plurality of first connectors are coupled directly to the at least one connector/screw head of the first spinal fixation assembly; and
the second second spinal fixation assembly comprises a spinal rod coupled to at least one connector/screw head, and the plurality of second connectors are coupled directly to the at least one connector/screw head of the second spinal fixation assembly.

4. The posterior spinal device of claim 3, wherein:
the first longitudinal slot that is parallel with the first lateral side of the plate; and
the second longitudinal slot that is parallel with the second lateral side of the plate.

5. The posterior spinal device of claim 1, wherein:
the first set of retention connectors comprising a first connector and a second connector;
the second set of retention connectors comprising a third connector and a fourth connector;
the first flange further comprises a first longitudinal groove on an underside thereof configured for receipt of the plurality of first connectors; and
the second flange further comprises a second longitudinal groove on an underside thereof configured for receipt of the plurality of second connectors;
wherein the plurality of first connectors engage the upperside of the first flange and extend through the first elongated slot and the first longitudinal groove to couple the first flange to the first spinal fixation assembly;

wherein the plurality of second connectors engage the upper-side of the second flange and extend through the second elongated slot and the second longitudinal groove to couple the second flange to the second spinal fixation assembly.

6. The posterior spinal device of claim 1, wherein:

first flange includes a first longitudinal groove on an underside thereof configured for receipt of a component of the first spinal fixation assembly; and the second flange includes a second longitudinal groove on an underside thereof configured for receipt of a component of the second spinal fixation assembly.

7. The posterior spinal device of claim 1, wherein:

the first longitudinal groove extends from a superior end to an inferior end of the first flange; and the second longitudinal groove extends from a superior end to an inferior end of the second flange.

8. The posterior spinal device of claim 1, wherein the plate, the first flange and the second flange have a superior/inferior curvature.

9. The posterior spinal device of claim 1, wherein the plate, the first fixation element and the second fixation element each define a superior end and an inferior end, and the superior/inferior curvature is a lordotic curvature.

10. A posterior spinal device attached to a first lateral posterior side of a plurality of vertebrae and to a second lateral posterior side of the vertebrae, the posterior spinal system comprising:

a first spinal fixation assembly coupled to the first lateral posterior side of the plurality of vertebrae;

a second spinal fixation assembly coupled to the first lateral posterior side of the plurality of vertebrae;

a plate having a first lateral side, a second lateral side, a superior side, and an inferior side, the plate sized to provide a surface between the first lateral side, the second lateral side, the superior side, and the inferior side, and to extend between the positioned first and second posterior lateral sides of the plurality of vertebrae, the plate at a first height;

a first flange substantially co-planar to the plate at a second height that is lower in an anterior direction than the first height, the first flange having a plurality of first connectors that attach the first flange to the first spinal fixation assembly anchored to the first posterior lateral side of the plurality of vertebrae, the first flange comprising a first elongated slot extending therethrough; and a second flange the inferior side and substantially co-planar to the plate at the second height, the second flange having a plurality of second connectors that attach the second flange to the second spinal fixation assembly anchored to the second posterior lateral side of the plurality of vertebrae, the second flange comprising a second elongated slot extending therethrough;

a first curved side member having a first end formed as a generally 90 degree bend in a first direction and a second end formed as a generally 90 degree bend in a second direction opposite the first direction to connect the first flange to the first lateral side of the plate a second curved side member having a first end formed as a generally 90 degree bend in a first direction and a second end formed as a generally 90 degree bend in a second direction opposite the first direction to connect the second flange to the second lateral side of the plate;

a plurality of first connectors extending through the first elongated slot to couple the plate to the first spinal fixation assembly at a plurality of positions along the first flange;

a plurality of second connectors extending through the second elongated slot to couple the plate to the second spinal fixation assembly at a plurality of positions along the second flange;

wherein the first direction of the first end of the first curved side member is opposite the first direction of the first end of the second curved side member, and the second direction of the second end of the first curved side member is opposite the second direction of the second end of the second curved side member.

11. The posterior spinal device of claim 10, wherein the plate is sized to extend between first and second posterior lateral sides of plurality of vertebrae to at least partially cover the vertebrae.

12. The posterior spinal device of claim 10, wherein the plate, the first flange and the second flange have a superior/inferior curvature.

13. The posterior spinal device of claim 10, wherein the plate, the first flange and the second flange each define a superior end and an inferior end, and having a superior/inferior lordotic curvature.

14. The posterior spinal device of claim 10, wherein:

the first flange has a first longitudinal groove on an underside thereof that extends from a superior end to an inferior end of the first flange; and the second flange has a second longitudinal groove on an underside thereof that extends from a superior end to an inferior end of the second flange;

wherein the plurality of first connectors engage the upper-side of the first flange and extend through the first slot to couple the first flange to the first spinal fixation assembly;

wherein the plurality of second connectors engage the upper-side of the second flange and extend through the second slot to couple the second flange to the second spinal fixation assembly.

15. The posterior spinal device of claim 10, wherein the plate is formed of a biocompatible plastic.

* * * * *